United States Patent
Hirsch et al.

(10) Patent No.: US 8,529,256 B2
(45) Date of Patent: Sep. 10, 2013

(54) AIR WATER VACUUM SYRINGE AND METHOD OF USE

(75) Inventors: James A. Hirsch, Santa Barbara, CA (US); Thomas R. Hirsch, Malibu, CA (US)

(73) Assignee: Innerlite, Inc., Santa Barbara, CA (US)

(*) Notice: Subject to any disclaimer, the term of this patent is extended or adjusted under 35 U.S.C. 154(b) by 221 days.

(21) Appl. No.: 12/939,943

(22) Filed: Nov. 4, 2010

(65) Prior Publication Data

US 2012/0003603 A1    Jan. 5, 2012

Related U.S. Application Data

(60) Provisional application No. 61/258,546, filed on Nov. 5, 2009.

(51) Int. Cl.
*A61C 17/06* (2006.01)
*A61C 17/12* (2006.01)

(52) U.S. Cl.
USPC .............................. 433/91; 433/95

(58) Field of Classification Search
USPC ............ 433/32, 80, 82, 84, 85, 87, 88, 91, 433/92, 95, 96, 98, 99, 100; 604/27, 32, 604/35, 119, 247, 248, 902; 600/156; 251/208, 251/304, 309, 311, 313, 330, 336, 206, 207; 137/565.13, 565.23
See application file for complete search history.

(56) References Cited

U.S. PATENT DOCUMENTS

| | | | | |
|---|---|---|---|---|
| 2,874,470 | A * | 2/1959 | Richards | 433/85 |
| 2,885,782 | A * | 5/1959 | Groves | 433/95 |
| 2,987,078 | A * | 6/1961 | Du Perow | 137/599.17 |
| 3,208,145 | A * | 9/1965 | Turner | 433/95 |
| 3,360,007 | A * | 12/1967 | Haidek et al. | 137/528 |
| 3,482,313 | A * | 12/1969 | Stram | 433/92 |
| 3,727,310 | A | 4/1973 | Baker | |
| 4,249,899 | A * | 2/1981 | Davis | 433/32 |
| 5,474,450 | A | 12/1995 | Chronister | |
| 5,546,985 | A * | 8/1996 | Bartholomew | 137/614.04 |
| 5,882,194 | A * | 3/1999 | Davis et al. | 433/29 |
| 6,159,007 | A * | 12/2000 | Sorensen | 433/80 |

(Continued)

FOREIGN PATENT DOCUMENTS

| | | | |
|---|---|---|---|
| KR | 10-0896415 | | 5/2009 |
| WO | WO 9508960 A1 | * | 4/1995 |

OTHER PUBLICATIONS

4 Way Overview, System Four Syringe, LL Dental, Blue River, OR.

(Continued)

*Primary Examiner* — Cris L Rodriguez
*Assistant Examiner* — Justin O'Donnell
(74) *Attorney, Agent, or Firm* — Stephen C. Beuerle; Procopio Cory Hargreaves & Savitch LLP

(57) ABSTRACT

An air water vacuum dental instrument includes a handle; a head; an air control carried by at least one of the handle and the head; a water control carried by at least one of the handle and the head; a vacuum control carried by at least one of the handle and the head; and an air water vacuum tip coupled to the head and configured to provide at least air, water, and vacuum in a mouth of a dental patient at the air water vacuum tip.

18 Claims, 20 Drawing Sheets

(56) References Cited

U.S. PATENT DOCUMENTS

| | | | |
|---|---|---|---|
| 6,203,321 B1* | 3/2001 | Helmer et al. | 433/95 |
| 6,464,498 B1 | 10/2002 | Pond | |
| 2007/0106204 A1* | 5/2007 | Fedenia et al. | 604/28 |
| 2008/0086835 A1* | 4/2008 | Stewen et al. | 15/347 |

OTHER PUBLICATIONS

Notification, International Search Report and Written Opinion for PCT/US2010/55501 dated Jul. 21, 2011.

* cited by examiner

AIR WATER VACUUM SYRINGE AND METHOD OF USE

FIELD OF THE INVENTION

The present invention relates to three way syringes (air, water, combo air water mist).

BACKGROUND OF THE INVENTION

In the past, dental professionals utilized two different dental instruments to aspirate fluid and other debris from a patient's mouth and add air/water to the patient's mouth. Because this required two hands to operate these two separate dental instruments, a dental assistant was required to perform the procedure or both of the dental professional's hands were occupied using these two separate dental instruments.

SUMMARY OF THE INVENTION

To solve these problems and others, the present invention involves an Air Water Vacuum (AWV) instrument that combines the air, water, combo air water mist features of a three way syringe with a suction aspirator into a single dental instrument. This invention will allow the dental professional to do with one hand what traditionally took two hands.

An aspect of the invention involves an air water vacuum dental instrument including a handle; a head; an air control carried by at least one of the handle and the head; a water control carried by at least one of the handle and the head; a vacuum control carried by at least one of the handle and the head; and an air water vacuum tip coupled to the head and configured to provide at least air, water, and vacuum in a mouth of a dental patient at the air water vacuum tip.

One or more implementations of the aspect of the invention described immediately above includes one or more of the following. The air water vacuum dental instrument includes a rotatable tip positioner that rotatably couples the air water vacuum tip to the head to provide at least air, water, and vacuum in a mouth of a dental patient at the air water vacuum tip. The vacuum control includes a high-flow vacuum condition, a low-flow vacuum condition, and a no-flow vacuum condition. The air water vacuum dental instrument includes a spring that urges the vacuum control to the no-flow condition. The air water vacuum dental instrument includes a valve carried by the head and a lever to control the valve. The valve includes a periphery with a pair of high-volume evacuator ports and a single saliva ejector port in communication with the pair of high-volume evacuator ports. The vacuum control includes a rotatable trigger valve barrel and a trigger carried by the handle, the trigger operably associated with the rotatable trigger valve barrel to rotate the trigger valve barrel to a different flow condition with each pull of the trigger. The vacuum control includes a high volume suction trigger and a lower volume evacuator toggle carried by the handle. The air water vacuum dental instrument includes a hose connected to the handle and delivering water and air therethrough, at least one of the hose, the handle, and the head including one or more heating elements to heat at least one of the water and the air. The air water vacuum dental instrument includes a heating lumen, an adjacent water lumen, and an adjacent air lumen, and the heating lumen includes one or more heating elements to heat the water in the water lumen and the air in the air lumen. The head is removably coupled to the handle. The air water vacuum dental instrument includes a quick-release mechanism that is actuatable to decouple the head from the handle. The head is at least one of sterilizable and autoclavable. The air water vacuum dental instrument includes an auto-shutoff mechanism that automatically shuts off the vacuum in the mouth of the dental patient. The auto-shutoff mechanism includes normal condition where a suction force overcomes an opposing force to allow the vacuum in the mouth of the dental patient and a shut-off condition where opposing force overcomes the suction force to shut off the vacuum in the mouth of the dental patient. The auto-shutoff mechanism includes at least one spring or magnet to provide the opposing force. The auto-shutoff mechanism includes at least two magnets to provide the opposing force. The air water vacuum tip is configured to bend at least one of water and air emitted at the tip. The air water vacuum tip includes a distal vertex, a proximate vertex with at least one of air and water emitted therefrom, and a vacuum port therebetween, at least one of water and air emitted at the distal vertex bending towards the vacuum port during vacuum. The air water vacuum tip includes a distal vertex with at least one of air and water emitted therefrom, a proximal vertex, and a vacuum port therebetween, at least one of water and air emitted straight at the distal vertex without bending towards the vacuum port during vacuum. The head is removably coupled to the handle and the air water vacuum dental instrument includes an automatic water shut-off valve mechanism that automatically shuts off water flow upon decoupling of the head from the handle and an automatic air shut-off valve mechanism that automatically shuts off air flow upon decoupling of the head from the handle.

BRIEF DESCRIPTION OF THE DRAWINGS

FIG. 13 is a perspective view of an embodiment of a base that the detachable head of the AWV instrument of FIG. 12 attaches to.

DETAILED DESCRIPTION OF PREFERRED EMBODIMENTS

Figure 1:
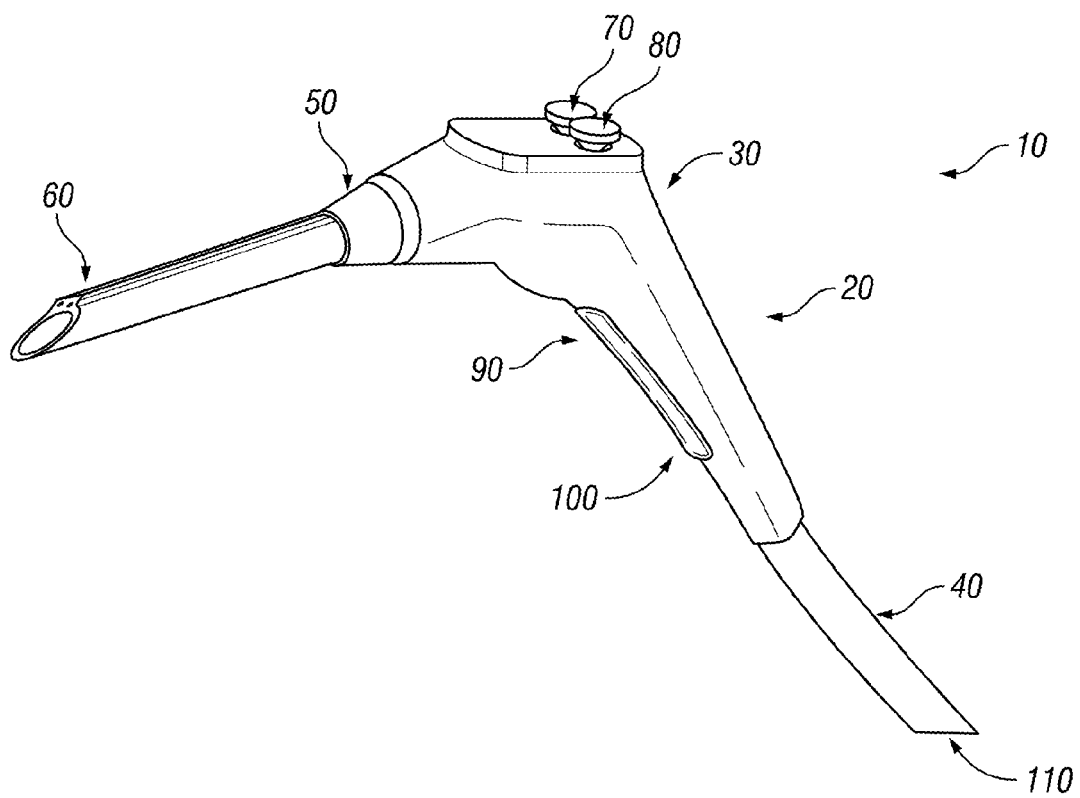
FIG. 1 is a perspective view of an embodiment of an Air Water Vacuum (AWV) instrument.

With reference to FIG. 1, an embodiment of an Air Water Vacuum (AWV) instrument 10 and method of using the same will be described. The AWV instrument 10 includes a handle/grip 20 with a head portion 30. A hose 40 extends from a bottom of the handle 20. A rotating tip positioner 50, which may be operated by a motor and controlled by a controller, extends from a front of the head portion 30. An elongated, tubular AWV tip 60 extends from and is rotated by the rotating tip positioner 50. Air and water buttons 70, 80 are disposed on a top of the head portion 30 for controlling air and/or water operation of the AWV instrument 10. The handle 20 includes a high volume suction trigger 90 and a lower volume evacuator toggle 100 on the trigger 90. One or more heating elements 110 may be disposed in the hose 40 for heating the water and/or air being delivered to the patient via the AWV instrument 10.

In one or more implementations of the AWV instrument 10, the AWV instrument 10 includes one or more of the following: the AWV tip 60 is disposable and/or autoclavable; trigger controlled activation of vacuum function through high volume suction trigger 90; trigger 90 includes locking feature to lock in the on position; AWV instrument 10 combines high volume suction and low volume functions within the same instrument operated with a toggle function on trigger 90; AWV instrument 10 combines automatic suction relief valve or auto off feature in case of tissue being sucked into AWV tip 60; hose 40 includes heated air and water included; AWV instrument 10 is used for tongue retraction and low volume aspiration simultaneously; the hose 40 is a single hose with multiple lumens; the AWV instrument 10 is installed on one or both the doctor and assistant tool stations per operator; and/or rotating tip positioner 50 allows suction from any angle without aspirating soft tissue into tip 60.

In use, the AWV instrument 10 delivers air, water, and combo air water mist to the patient by actuating the air/water buttons 70, 80 with one's thumb. Operation of the trigger 90 with one's fingers of same hand controls aspiration. Toggle 100 enables low volume aspiration or high volume aspiration of fluid and other debris from the patient's mouth in a single instrument. The heating element(s) 110 warms the water/air delivered to the patient's mouth.

Thus, the AWV instrument 10 allows the dental professional to do with one hand what traditionally took two hands. The AWV instrument 10 greatly reduces the amount of tubing and clutter in dental operating area. The pistol type design provides better leverage and comfort for extended retraction procedures, reducing the potential for repetitive stress injuries. The AWV instrument 10 will give dentist and assistant a much needed third hand or allow a solo practitioner to be more efficient.

Figure 2A:
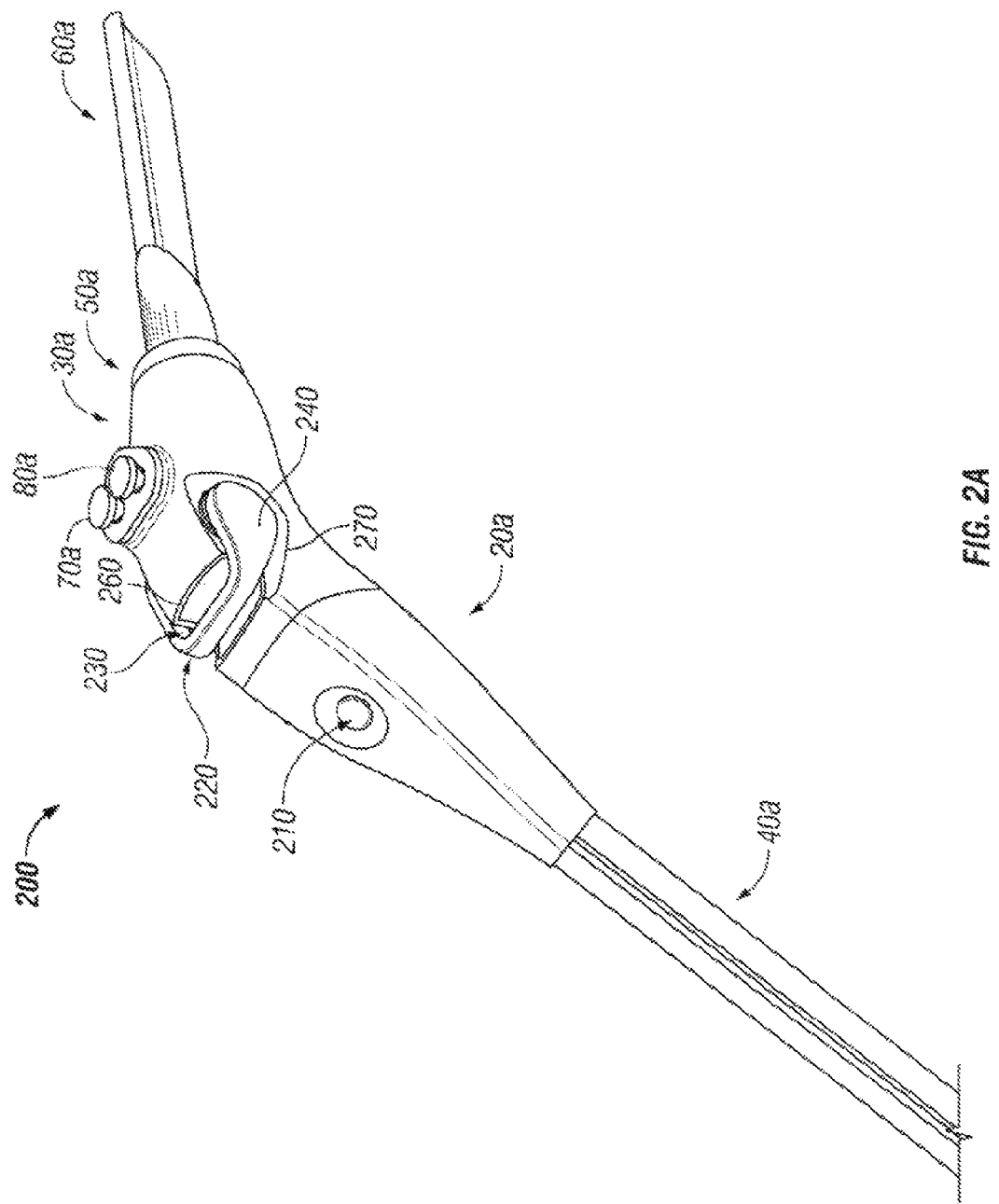
FIG. 2A is a rear perspective view of another embodiment of an AWV instrument.
Figure 2B:
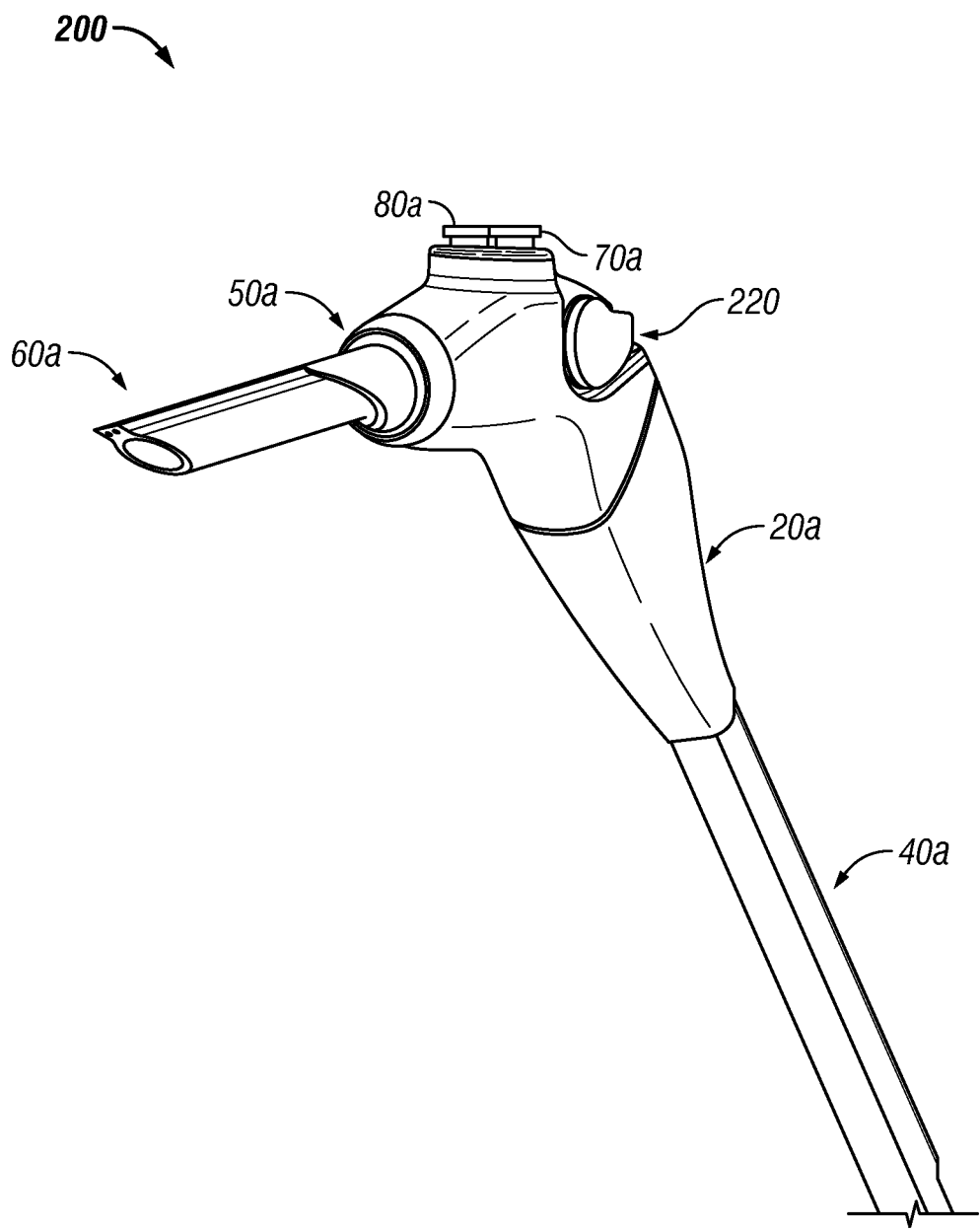
FIG. 2B is a front perspective view of the AWV instrument of FIG. 2A.

With reference to FIGS. 2A and 2B, another embodiment of an AWV instrument 200 will be described. The elements of the AWV instrument 200 that are similar to the AWV instrument 10 described above will be identified with like references numbers, but with a letter suffix. The above description of the AWV instrument 10 is incorporated herein. The AWV instrument 200 is similar to the AWV instrument 10, except that the AWV instrument 200 includes a quick-release button/mechanism 210 on a back/rear side of the handle/grip 20a that, when actuated, disengages/unlocks the head portion 30a from the handle/grip 20a. The quick release button/mechanism 210 may include a latch or other locking mechanism that is lockable/unlockable for attaching/detaching the head portion 30a from the handle/grip 20a. As in the previous embodiment, AWV instrument 200 has a hose 40a extending from the bottom of handle 20a, a rotating tip positioner 50a, and air/water buttons 70a and 80a.

Figure 18A:
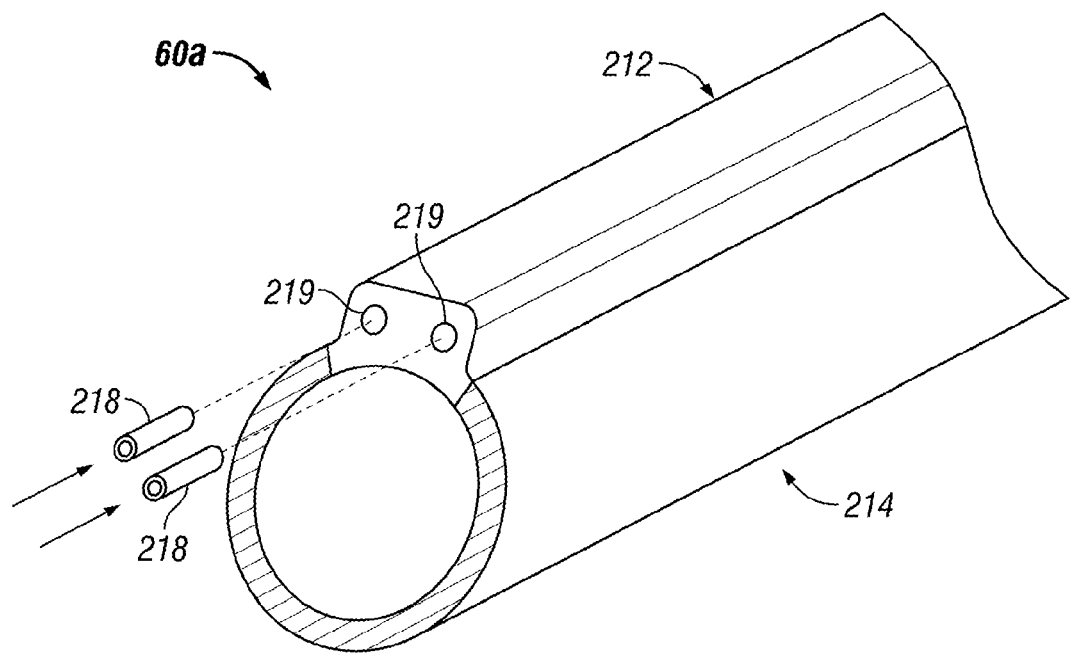
FIG. 18A is a perspective view of a proximal end portion of an embodiment of an AWV tip of the AWV instrument with water and air supply pins shown separate from the tip and aligned with pin receiving bores in the tip.
Figure 18B:
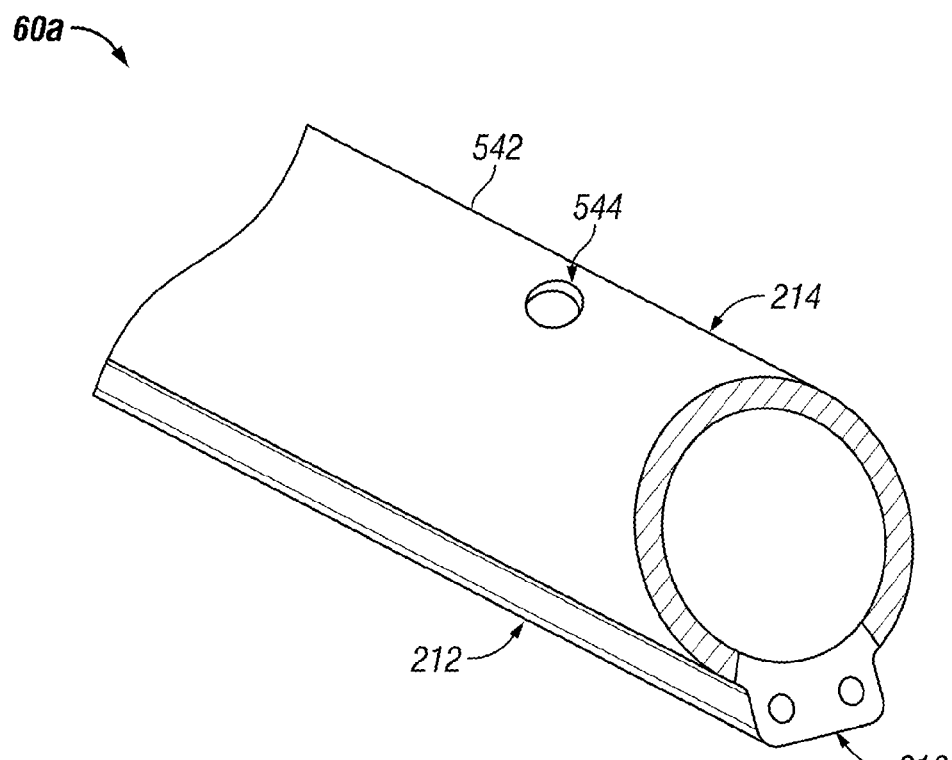
FIG. 18B is a perspective view of the distal end portion of the AWV tip of FIG. 18A.

With reference to FIGS. 2B, 18A, and 18B, the elongated, tubular AWV tip 60a includes an elongated soft-rubber coextrusion member 212 and an elongated hard plastic base tube 214 with a "C" shaped cross section. The elongated soft-rubber coextrusion member 212 includes a distal protrusion 216 made of soft rubber or other flexible material to protection oral tissue. The distal portion 216 would normally be sharp if using a hard material such as the material of the plastic base tube 214, but because of the soft-rubber coextrusion member 212, a soft tip is created after cutting the end of the tip 60a during manufacture for patient comfort. Hollow pins 218 bring water and air into tip 60a. The pins 218 are matingly received in elongated lumens 219 of the elongated soft-rubber coextrusion member 212 and are sealingly engaged therein (soft rubber seals around pins 218, preventing leaking).

Figure 3A:
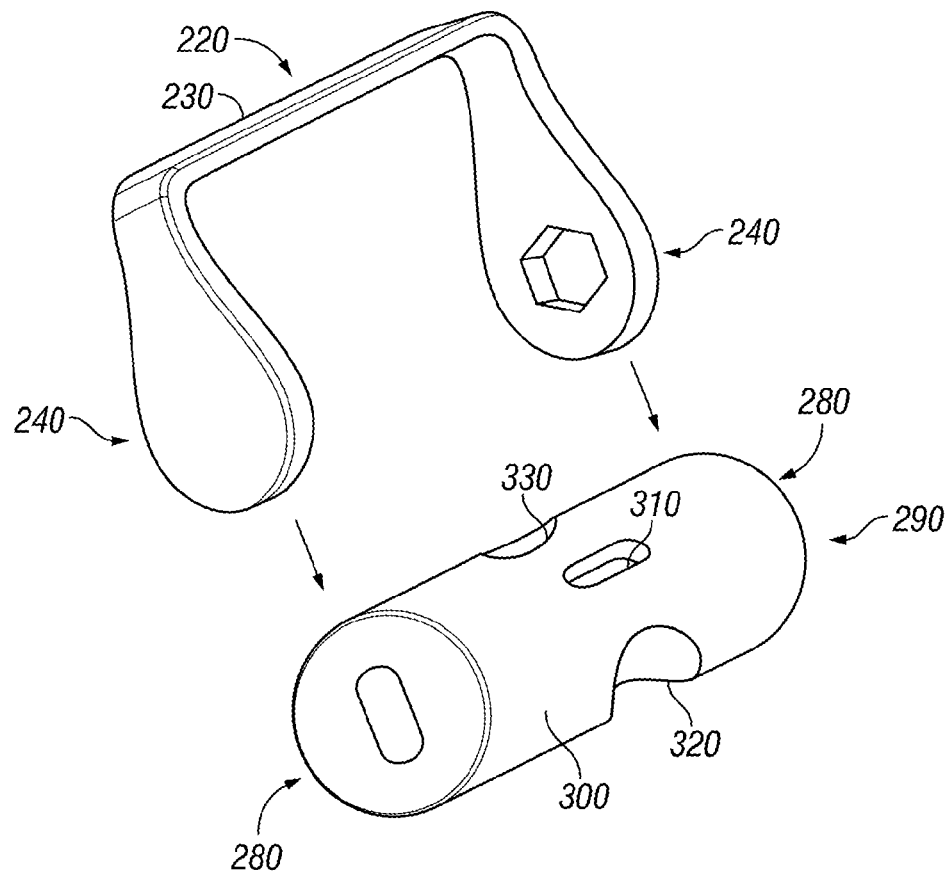
FIG. 3A is a perspective view of an embodiment of an activation lever and a four-way syringe of the AWV instrument.
Figure 5A:
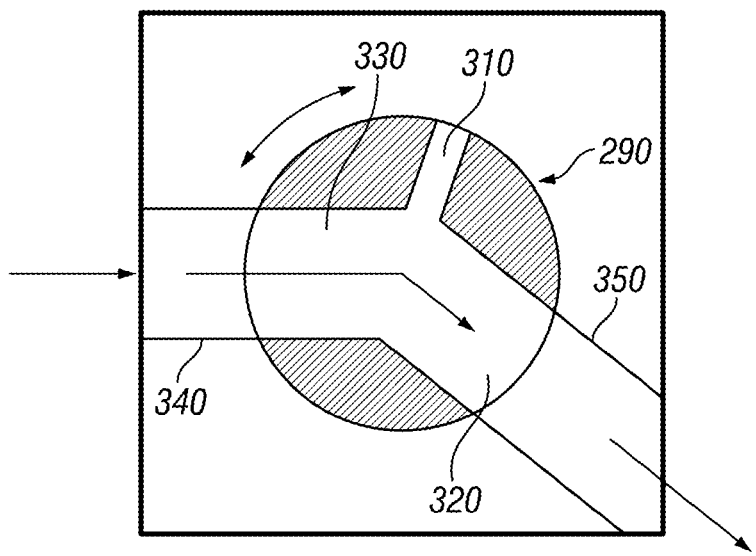
FIG. 5A illustrates an open position of the four-way syringe of the AWV instrument.
Figure 5B:
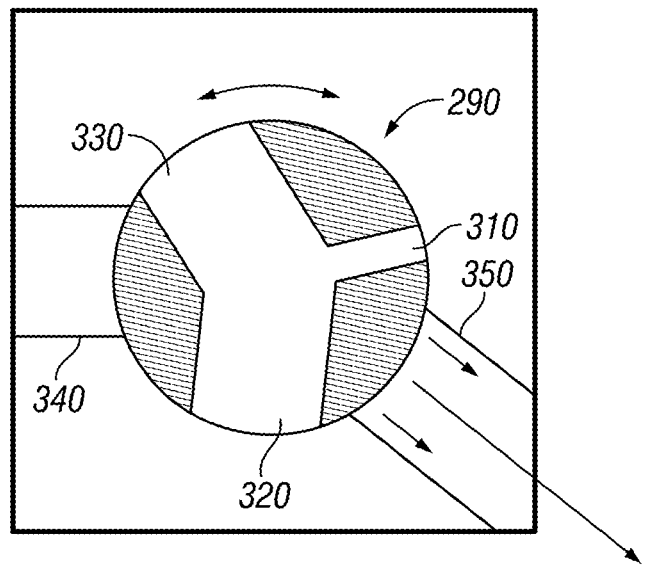
FIG. 5B illustrates a closed or no-flow position of the four-way syringe of the AWV instrument.
Figure 5C:
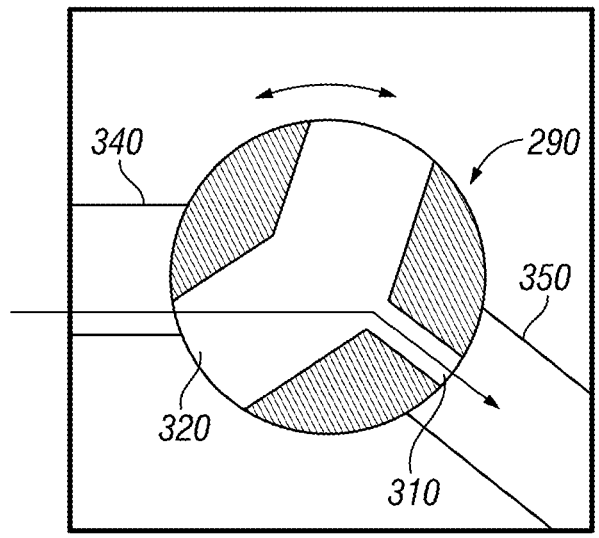
FIG. 5C illustrates a saliva ejection position of the four-way syringe of the AWV instrument.

Another difference with the AWV instrument 200 is that instead of high volume suction trigger 90 and lower volume evacuator toggle 100 as with the AWV instrument 10, the AWV instrument 200 includes an activation lever 220 that controls/moves a valve (FIG. 3A) in the head portion 30a between at least a high-flow vacuum condition (FIG. 5A), a no-flow saliva ejection condition (FIG. 5B), and a low-flow saliva ejection condition (FIG. 5C). With reference additionally to FIG. 3A, the activation lever 220 includes a bridge 230 that couples opposite lobe-shaped ends 240 together. In the position shown in FIG. 2A, the bridge 230 is disposed in a laterally extending top recess 260 on a rear of the head portion 30a and the ends 240 are disposed in opposite side recesses 270 of the head portion 30a.

As shown in FIG. 3A, the ends 240 of the activation lever 220 are connected to opposite ends 280 of substantially cylindrical saliva ejector valve 290 for connecting the lever 220 to the valve 290. Along a periphery 300 of the valve 290 are saliva ejector port 310 and high-volume evacuator ports 320, 330. As shown in FIGS. 5A-5C, movement of activation lever 220 causes the valve 290 to move from a high-flow vacuum condition, where high-volume evacuator ports 320, 330 are in full communication with communication passages 350, 340 and saliva ejector port 310 is blocked (FIG. 5A), to a no-flow saliva ejection condition, where high-volume evacuator ports 320, 330 and saliva ejector port 310 are blocked from communication with communication passages 350, 340 (FIG. 5B), and to a low-flow saliva ejection condition, where high-volume evacuator port 320 is in partial communication with communication passage 340, saliva ejector port 310 is in full communication with communication passage 350, and high-volume evacuator port 330 is blocked (FIG. 5C).

Figure 3B:
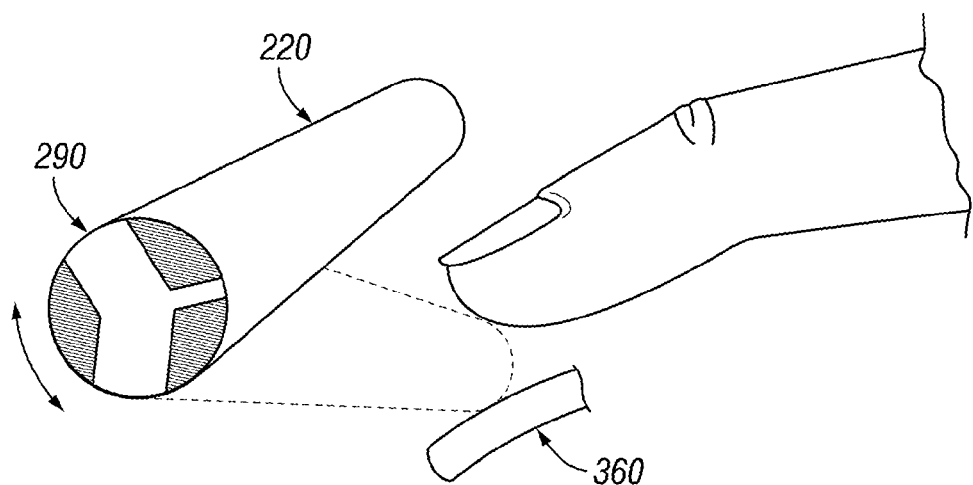
FIG. 3B is side-elevational view of the activation lever of FIG. 3A.
Figure 4:
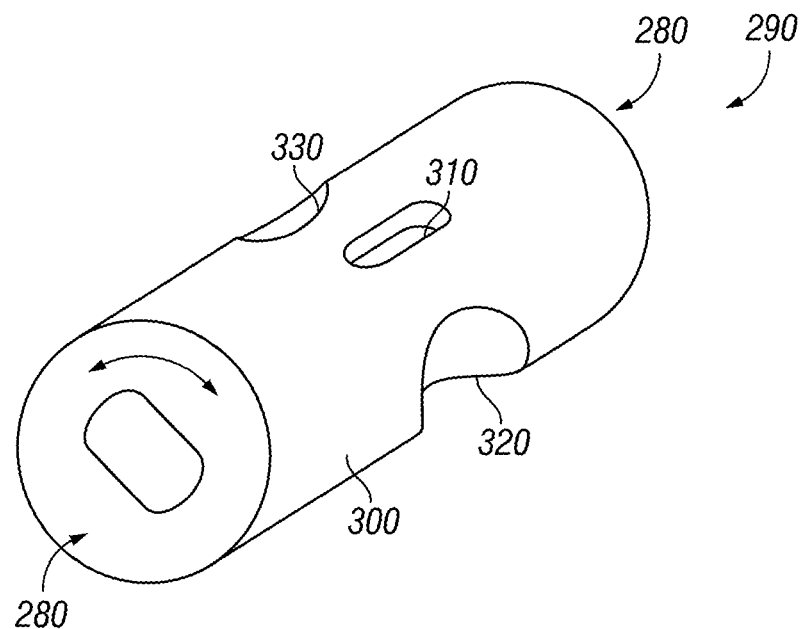
FIG. 4 is a perspective view of the valve barrel shown in FIG. 3A.

As shown in FIG. 3B, a spring tab/plunger 360 biases the valve 290 via the lever 220 towards the no-flow/closed condition (FIG. 5B).

With reference to FIGS. 17A-17E, another embodiment of lever and valve assembly 362 will be described. The assembly 362 includes valve 290a, auto-shutoff and auto adjustment slides 364, magnets 366, C-ring 368, retainer ring 370, retainer ring (with stops) 372, main lever 374, return arm 376, return spring 378, and return assembly cap 380.

Figure 17A:
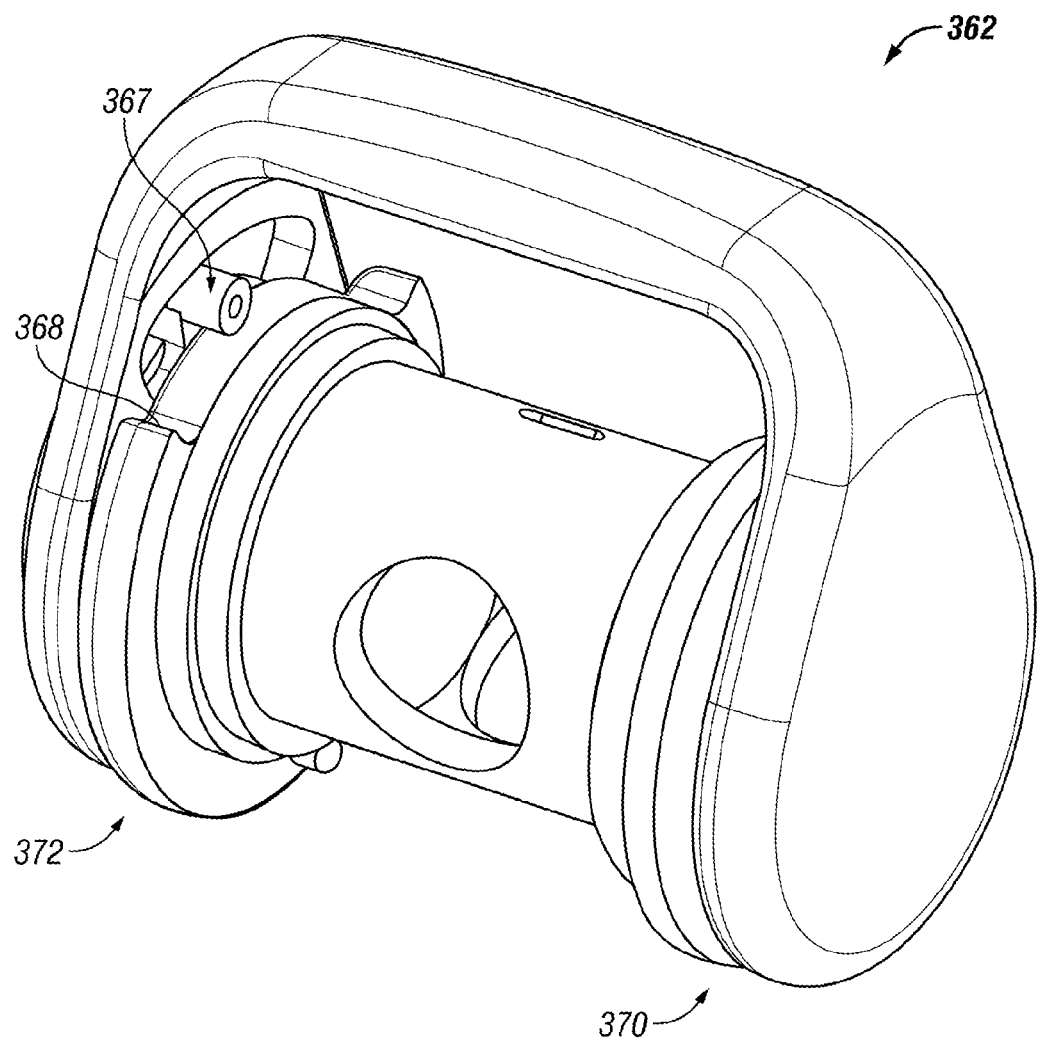
FIG. 17A is a perspective view of another embodiment of a lever and valve assembly, illustrating a saliva ejector spring back mechanism.

FIG. 17A shows the saliva ejector spring back mechanism 367 (i.e., same function as spring finger 360 in FIG. 3B) and stop 368 for the spring lever/of L-shaped member 394. The retainer rings 370, 372 are mounted on a housing of the head portion. The valve lever 374 is removable for cleaning.

Figure 17B:
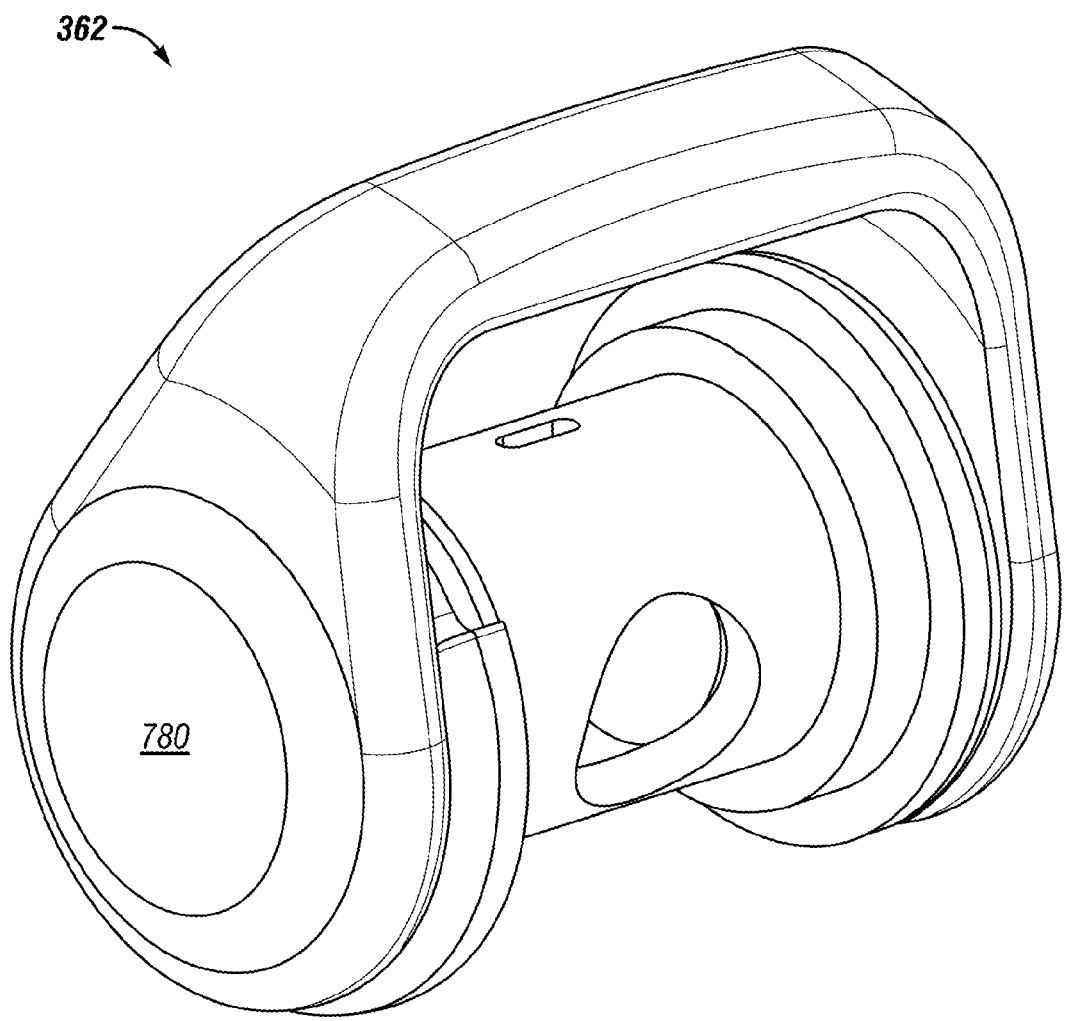
FIG. 17B is a perspective view of the lever and valve assembly of FIG. 17A from a different direction, illustrating a return assembly cap that covers a return spring of the assembly.

FIG. 17B shows the return assembly cap 380 that covers the return spring 378.

Figure 17C:
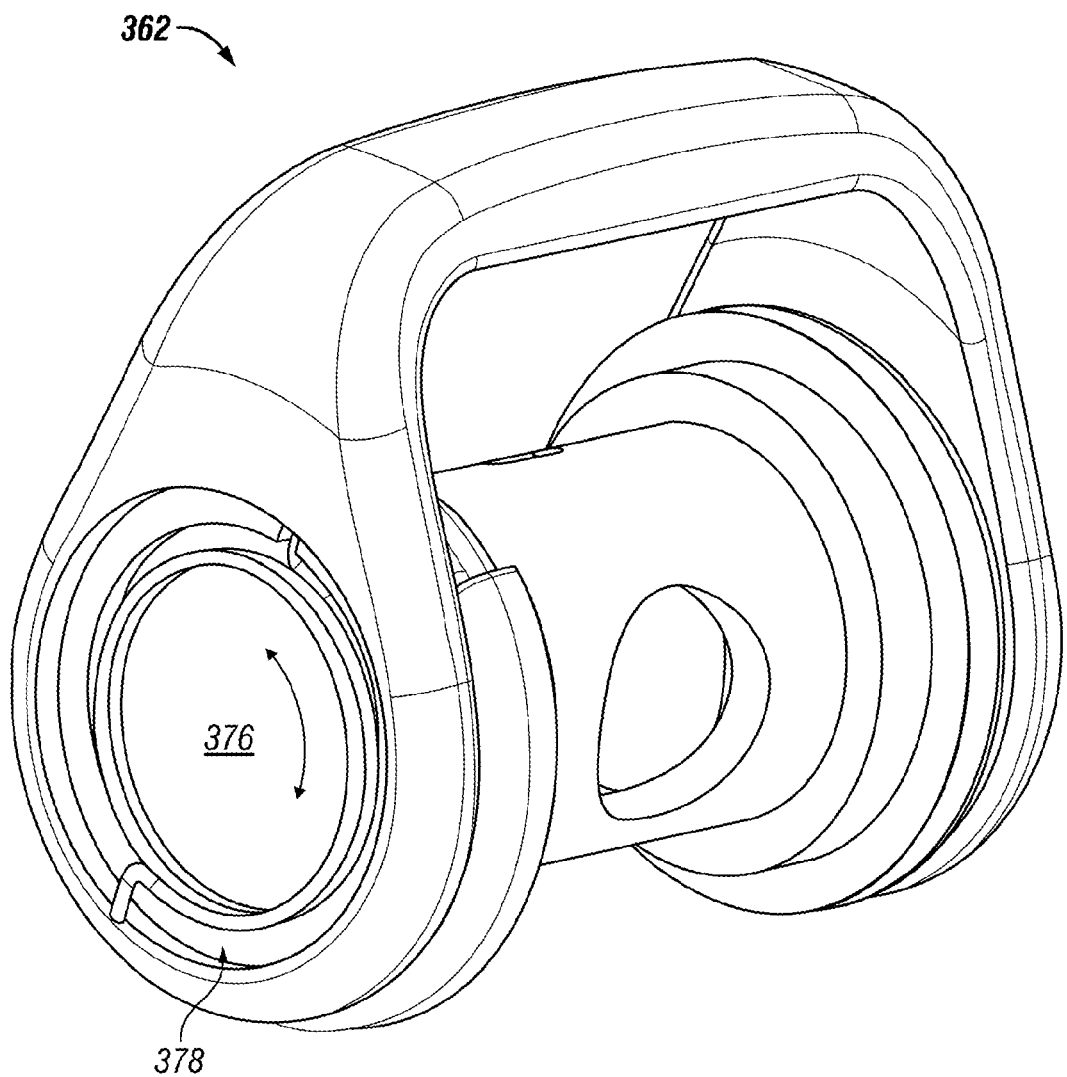
FIG. 17C is a perspective view similar to FIG. 17B but with the cap removed to reveal the return spring and return arm.

FIG. 17C shows the return spring 378 and the return arm 376 that rotates within the housing.

Figure 17D:
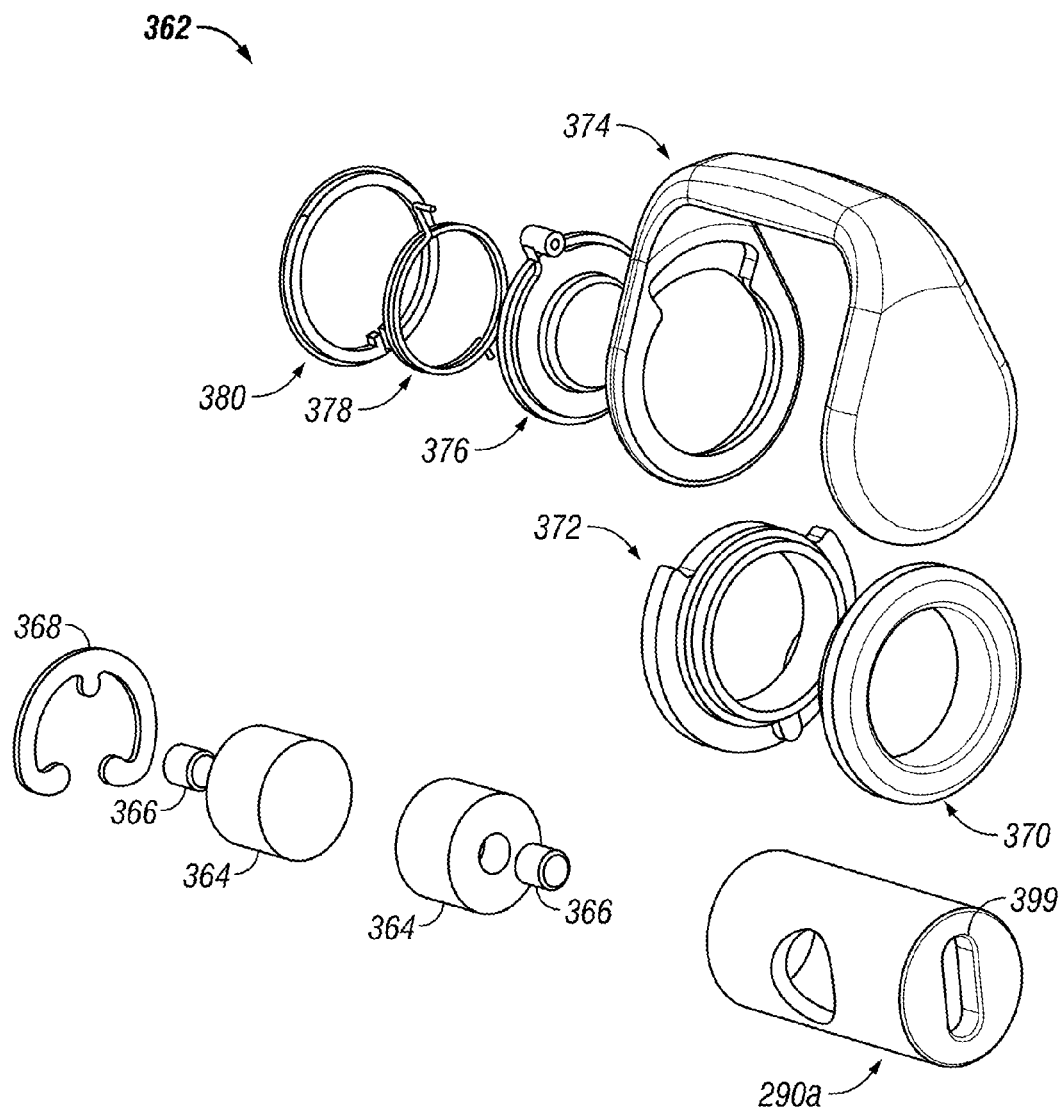
FIG. 17D is an exploded perspective view of the lever and valve assembly of FIGS. 17A to 17C, illustrating the separate parts of the assembly.
Figure 17E:
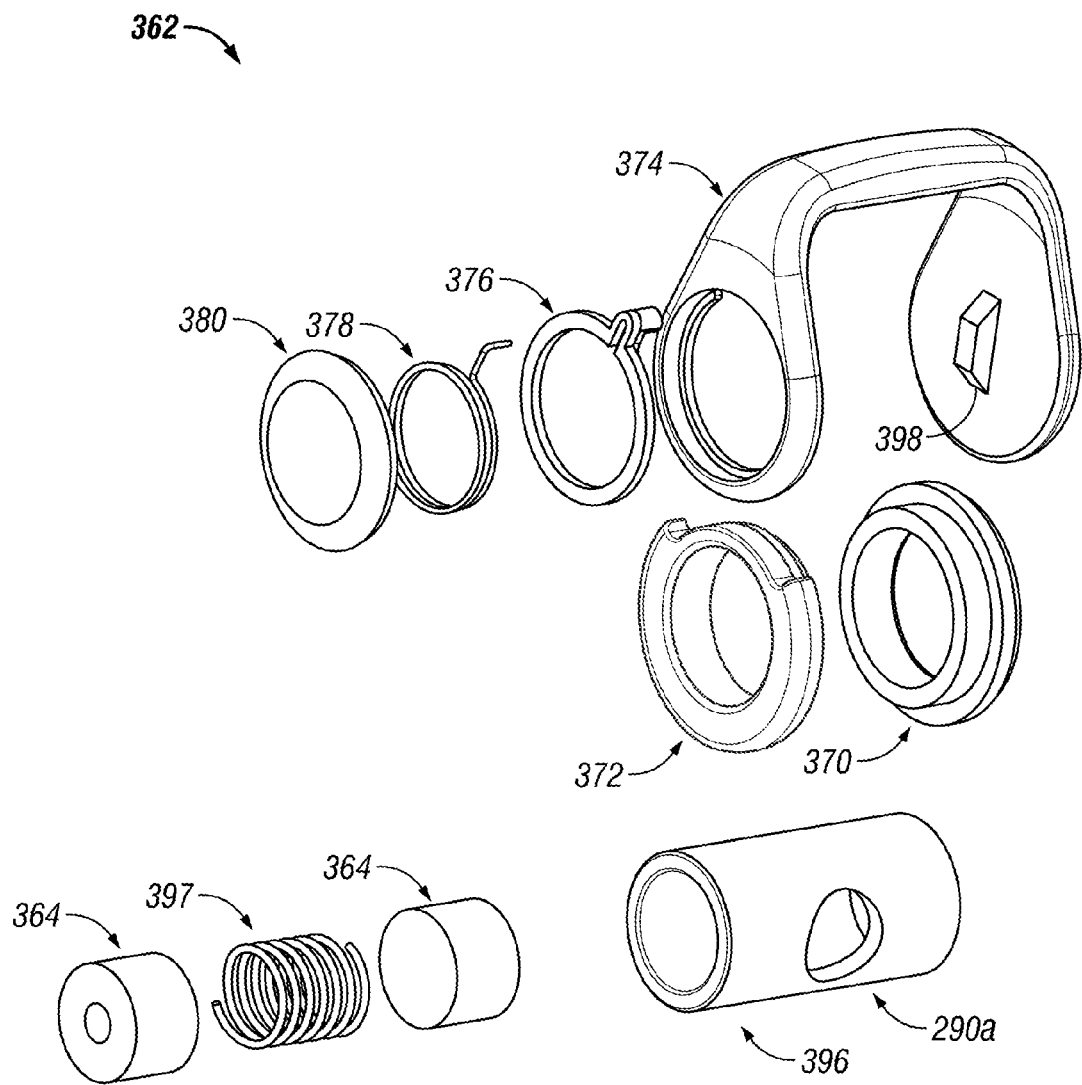
FIG. 17E is an exploded perspective view similar to FIG. 17D, but illustrating an alternative embodiment of the auto-shut off and auto adjustment slide assembly which replaces the return spring of the embodiment of FIGS. 17A to 17D.

With reference to FIG. 17D, along a periphery 382 of the valve 290 are saliva ejector port 310a and high-volume evacuator ports 320a, 330a. The valve 290 includes a cut-through for free air access. The C-ring 368 holds the assembly in place. The retainer ring (with stops) 372 includes a key 384 to keep stops 386 in position. The return arm 376 includes an inwardly extending disc-shaped member 388 that rotates freely on valve 290a, allowing the return arm 376 to rotate, pushing back to off position when return assembly cap 380 is released. As shown in FIG. 17E, the spring 378 includes a L-shaped arm 390 that extend into a hole 392 of L-shaped member 394 of return arm 376.

FIG. 17E illustrates an alternative embodiment of an auto-shutoff and auto adjustment slide assembly 396 where the magnets 366 are replaced by a spring 397 for an alternative means of resistance between slides 364. Lever key 398 mates with hole 399 on an end of the valve 290a to drive the valve 290a.

Figure 6:
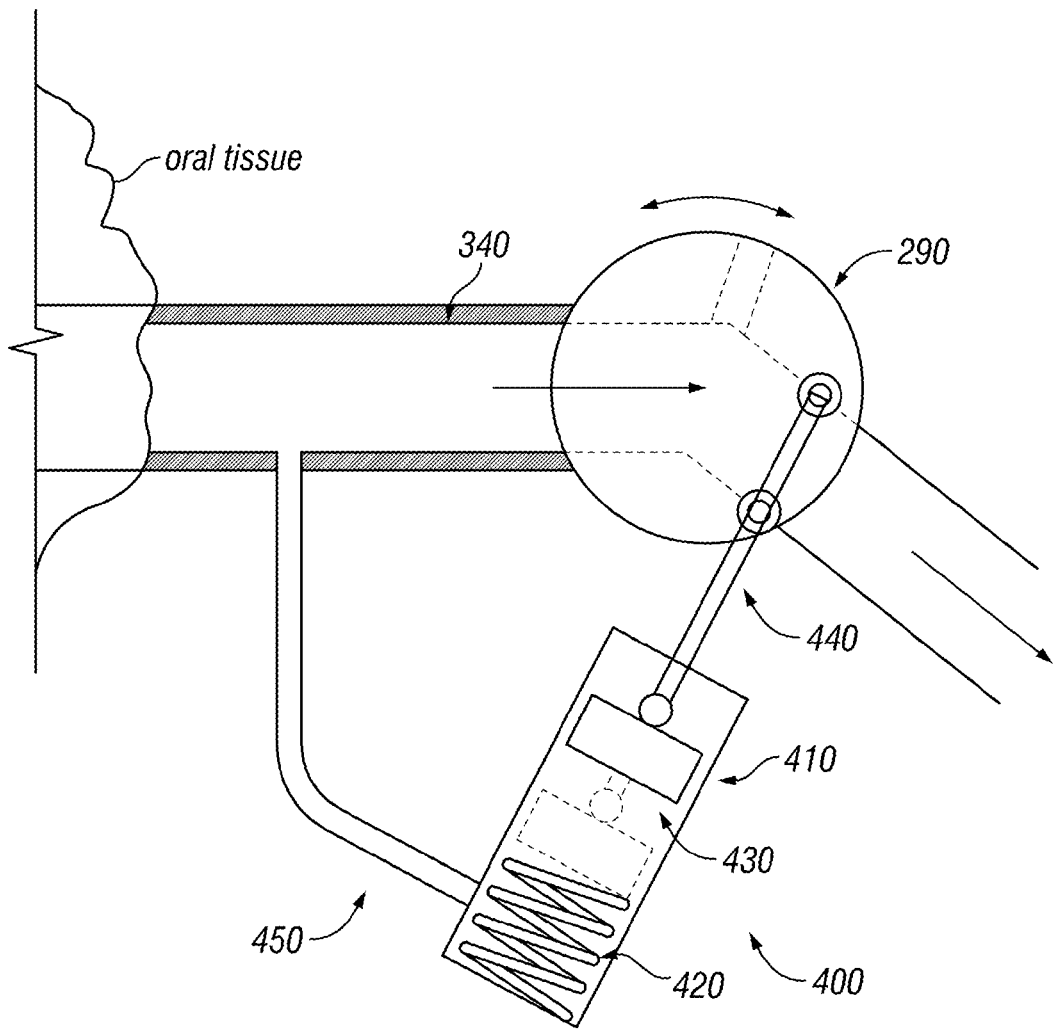
FIG. 6 is a cross-sectional view of an embodiment of the auto shutoff mechanism for the AWV instrument.

With reference to FIG. 6, an embodiment of an auto-shutoff mechanism 400 for the AWV instrument 10, 200 will be described. To assist the reader in understanding this aspect of the invention, the remainder of the AWV instrument 10, 200 is not shown. The auto-shutoff mechanism 400 includes a cylinder 410 with a spring 420 and piston 430 therein. The cylinder 410 is in communication with communication passage 340 via small suction tube 450. The piston 430 is mechanically coupled to the valve 290 via a shaft 440. During normal use, when an end of the AWV tip 60 is not blocked, vacuum flow occurs through the communication passage 340, which causes suction flow in the small suction tube 450. This suction flow in the small suction tube 450 draws the piston 430 downward into the cylinder 410, compressing the spring 420. If a blockage occurs at the AWV tip 60 (e.g., oral tissue is vacuumed into AWV tip 60), then the decrease/stopping of flow through the communication passage 340 causes suction flow in the small suction tube 450 to decrease/stop. The biasing force of the spring 430 pushing upwardly/outwardly on the piston 430 exceeds any countering suction force on the piston 430 from the small suction tube 450. Thus, the piston 430 and the shaft 440 move upward in the cylinder 410, causing the valve 290 to rotate to the closed position shown in FIG. 5B. With the valve 290 in the closed position, all suction force in the AWV tip 60 ceases so that oral tissue is no longer suctioned into he AWV tip 60. Normal use may resume by moving the valve 290 to the desired position via the lever 220.

Figure 15:
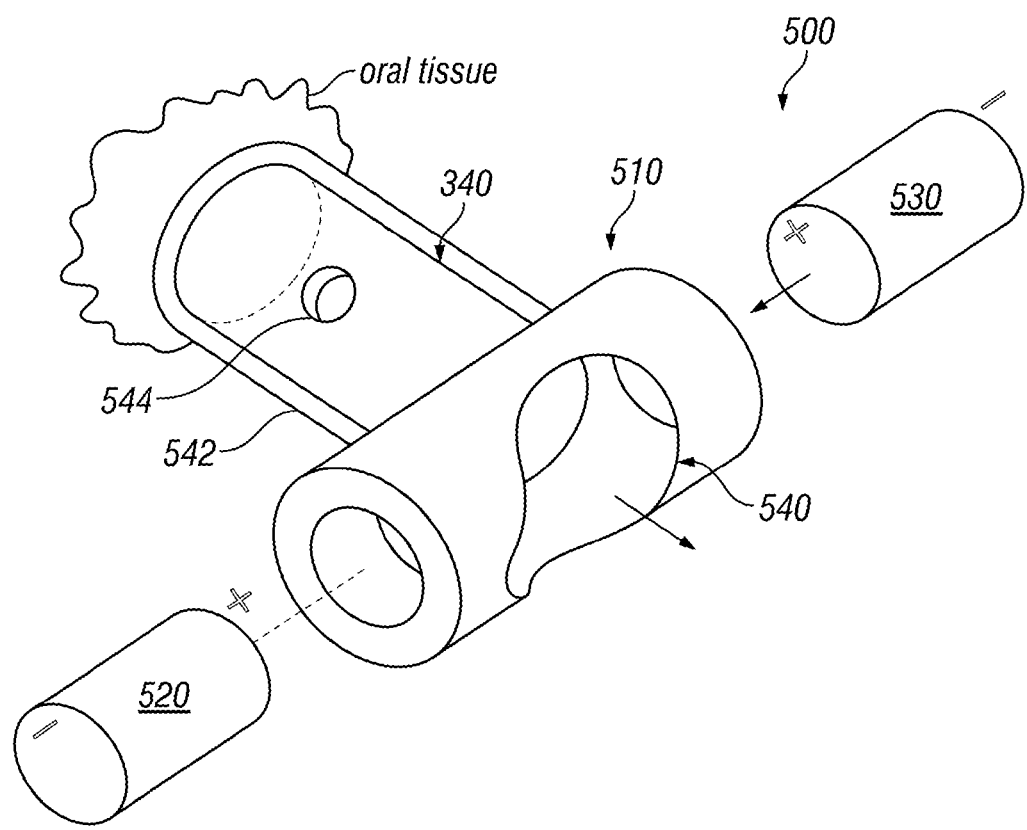
FIG. 15 is a perspective view of another embodiment of the auto shutoff mechanism for the AWV instrument.
Figure 16A:
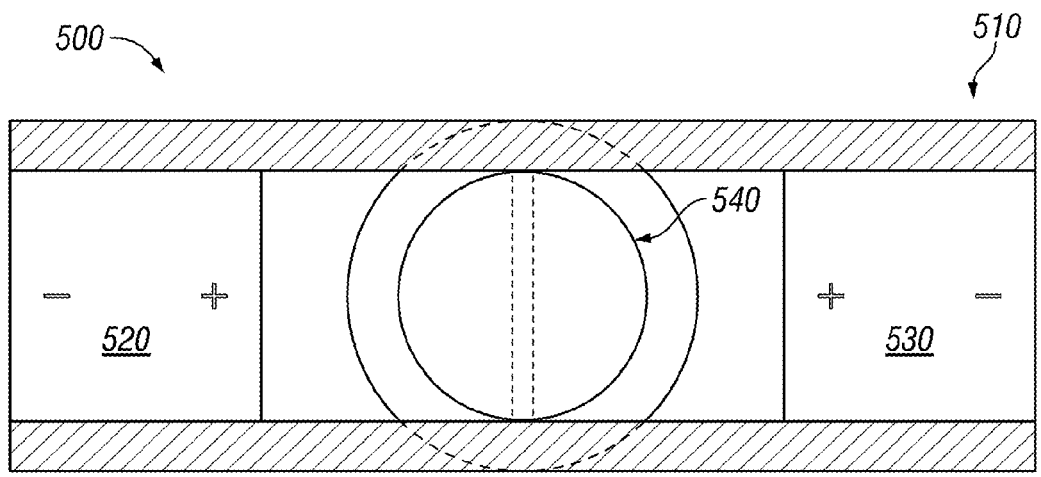
FIG. 16A is a cross-sectional view of the auto shutoff mechanism of FIG. 15 with an embodiment of an auto shutoff gate shown in an open position.
Figure 16B:
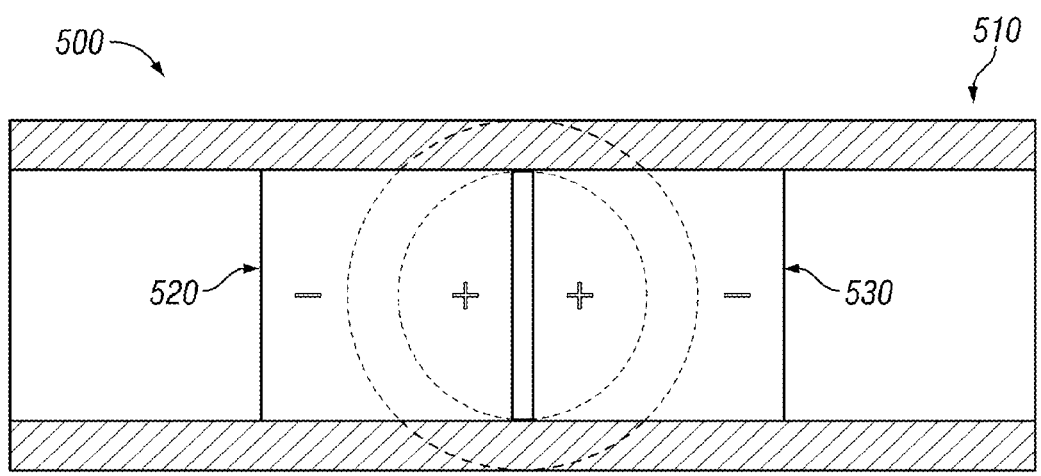
FIG. 16B is a cross-sectional view of the auto shutoff mechanism of FIG. 15 with the auto shutoff gate shown in a closed position.

With reference to FIG. 15, another embodiment of an auto-shutoff mechanism 500 for the AWV instrument 10, 200 will be described. Similar to FIG. 6, to assist the reader in understanding this aspect of the invention, the remainder of the AWV instrument 10, 200 is not shown. The auto-shutoff mechanism 500 includes a generally cylindrical valve barrel 510, which may be similar to the valve 290, with a cylindrical first auto-shutoff gate 520 and a cylindrical second auto-shutoff gate 530 slidably disposed therein. Each auto-shutoff gate 520, 530 may have a magnetic polarity such as that shown so that the like magnetic polarities causes a magnetic force that causes the gates 520, 530 to repel each other so that the gates are separated as shown in FIG. 16A. When the AWV tip 60 is blocked (e.g., oral tissue is vacuumed into AWV tip 60), then the suction force drawing the gates 520, 530 towards each other, to block opening(s) 540, overcomes the repelling magnetic force of the gates 520, 530 and the gates 520, 530 move to the position shown in FIG. 16B, where the gates 520, 530 block the opening(s) 540 so that suction force at the AWV tip 60 ceases. The oral tissue is no longer suctioned into the AWV tip 60. Normal use may resume (and opening of the gates 520, 530 to the position shown in FIG. 16A) by moving the valve barrel 510 to the desired position (e.g., off position, low volume evacuation position) via the lever 220. In an alternative embodiment, the auto-shutoff mechanism 500 may include only one auto-shutoff gate slidably disposed within the valve barrel 510 (e.g., one magnetic gate may move and another magnetic member may be fixed in valve barrel 510). With reference to FIGS. 15 and 18B, in an additional embodiment, a wall 542 defining communication passage 340 may include a hole 544 to release suction when the AWV tip 60 is plugged/obstructed.

Figure 7:
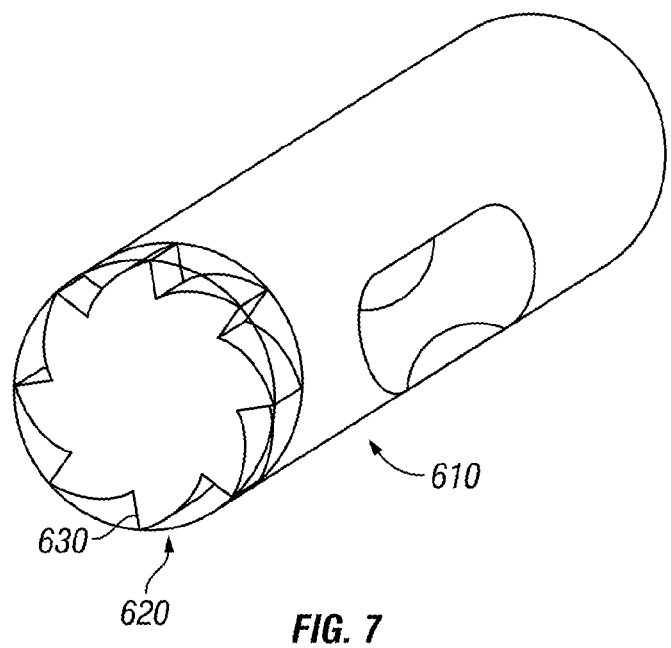
FIG. 7 is a perspective view of an embodiment of a trigger valve barrel of a trigger valve mechanism of the AWV instrument.
Figure 8:
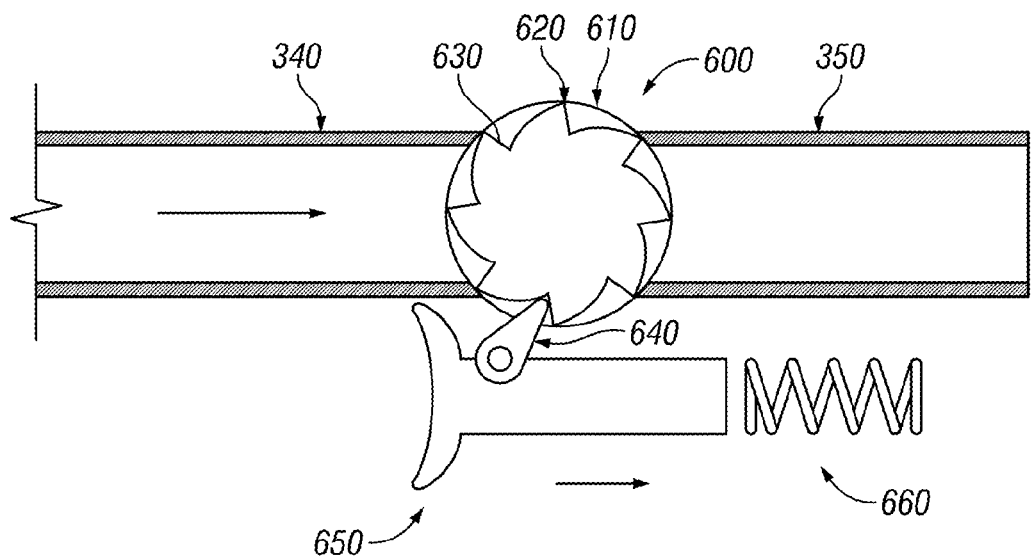
FIG. 8 is a side elevational view of an embodiment of a trigger valve mechanism of the AWV instrument.

With reference to FIGS. 7 and 8, an embodiment of a trigger valve mechanism 600 of the AWV instrument 10, 200 will be described. To assist the reader in understanding this aspect of the invention, the remainder of the AWV instrument 10, 200 is not shown. The trigger valve mechanism 600 includes a trigger valve barrel 610 similar to valve 290, except the trigger valve barrel 610 includes a ratchet 620 (simplified view of ratchet is shown) with saw tooth members 630 that are engaged by a pawl 640, which is hingeably connected to a trigger 650 and includes a spring (not shown) for spring return of the pawl 640. A trigger spring 660 urges the trigger 650 forward. In use, the trigger valve barrel 610 is advanced/rotated ¼ turn per trigger squeeze. In another embodiment, a single first pull of the trigger 650 rotates the trigger valve barrel 610 ninety degrees from open (e.g., FIG. 5A, 5C) to closed (FIG. 5B) to open (e.g., FIG. 5A, 5C) with a second pull. It is important to note that it is not necessary to hold the trigger 650 down/in during the suction procedure.

Figure 9:
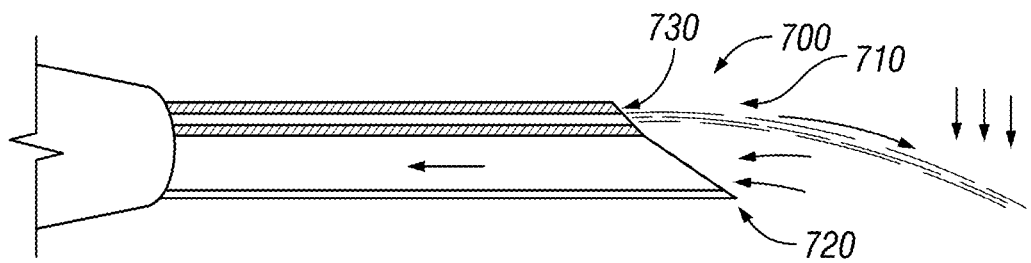
FIG. 9 is a cross-sectional view of an embodiment of a water spray bending tip of the AWV instrument.

With reference to FIG. 9, an embodiment of a water spray bending AWV tip 700 of the AWV instrument 10, 200 will be described. The AWV tip 700 includes a beveled end 710 with a distal angled vacuum opening 720 at a distal point/vertex and a proximal angled water/air opening 730 at a proximal point/vertex. In use, the suction intake at the distal angled vacuum opening 720 bends an emitted stream of water (or air or combination air/water) from the proximal angled water/air opening 730 (emulating a standard three-way syringe bent tip) without bending the tip.

Figure 10:
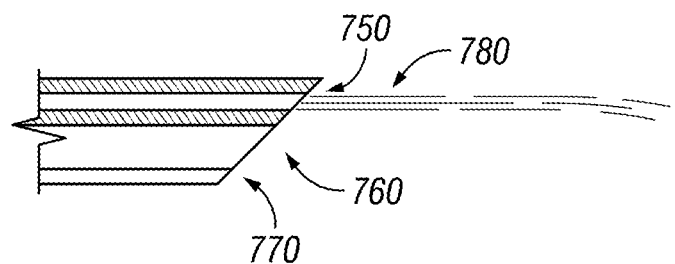
FIG. 10 is a cross-sectional view of an embodiment of a water spray tip of the AWV instrument.

With reference to FIG. 10, another embodiment of a water spray AWV tip 750 of the AWV instrument 10, 200 will be described. The AWV tip 750 includes a beveled end 760 with a proximal angled vacuum opening 770 at a proximal point/vertex and a distal angled water/air opening 780 at a distal point/vertex. Locating the air/water port(s) at top/distal point/vertex of angle produces a straight stream of water (or air or combination air/water).

In an alternative embodiment, a water spray AWV tip may include air/water port(s) at both a top/distal part of angle and a bottom/proximal part of angle (i.e. combination of embodiments shown in FIGS. 9 and 10).

Figure 11:
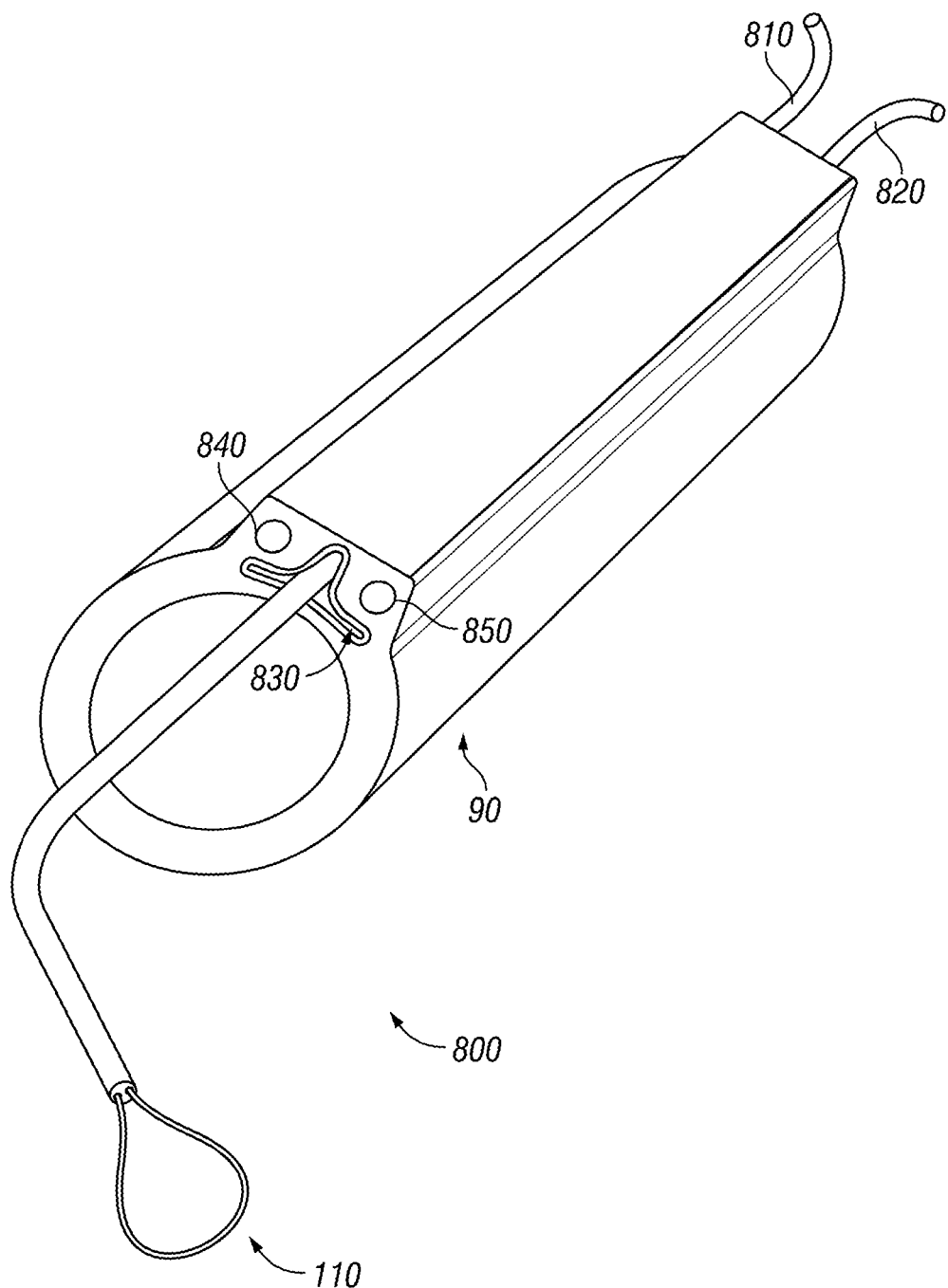
FIG. 11 is a perspective view of an embodiment of tube heating mechanism of the AWV instrument.

With reference to FIG. 11, an embodiment of tube heating mechanism 800 of the AWV instrument 10, 200 will be described. The tube heating mechanism 800 includes flexible resistance heating element 110 along with connected positive and negative wires 810, 820 disposed within a heating lumen 830 of extruded tube/hose 40. Because the heating lumen 830 (and heating element 110 therein) is adjacent to air lumen 840 and water lumen 850 of tube/hose 40, heat emitted from the heating element 110 heats air transmitted through air lumen 840 and water transmitted through water lumen 850. Warmed water/air transmitted through the tube/hose 40 into the patient's mouth via the AWV instrument 10, 200 increases the patient's comfort, especially if the patient has sensitive teeth/gums.

With reference to FIGS. 12-14B, an embodiment of an AWV instrument 900 including a detachable head 910 and embodiments of automatic shut-off valve mechanisms will be described. The elements of the AWV instrument 900 that are similar to the AWV instrument 10, 200 described above will be identified with like references numbers, but with a letter suffix. The above description of the AWV instrument 10, 200 is incorporated herein.

Figure 12:
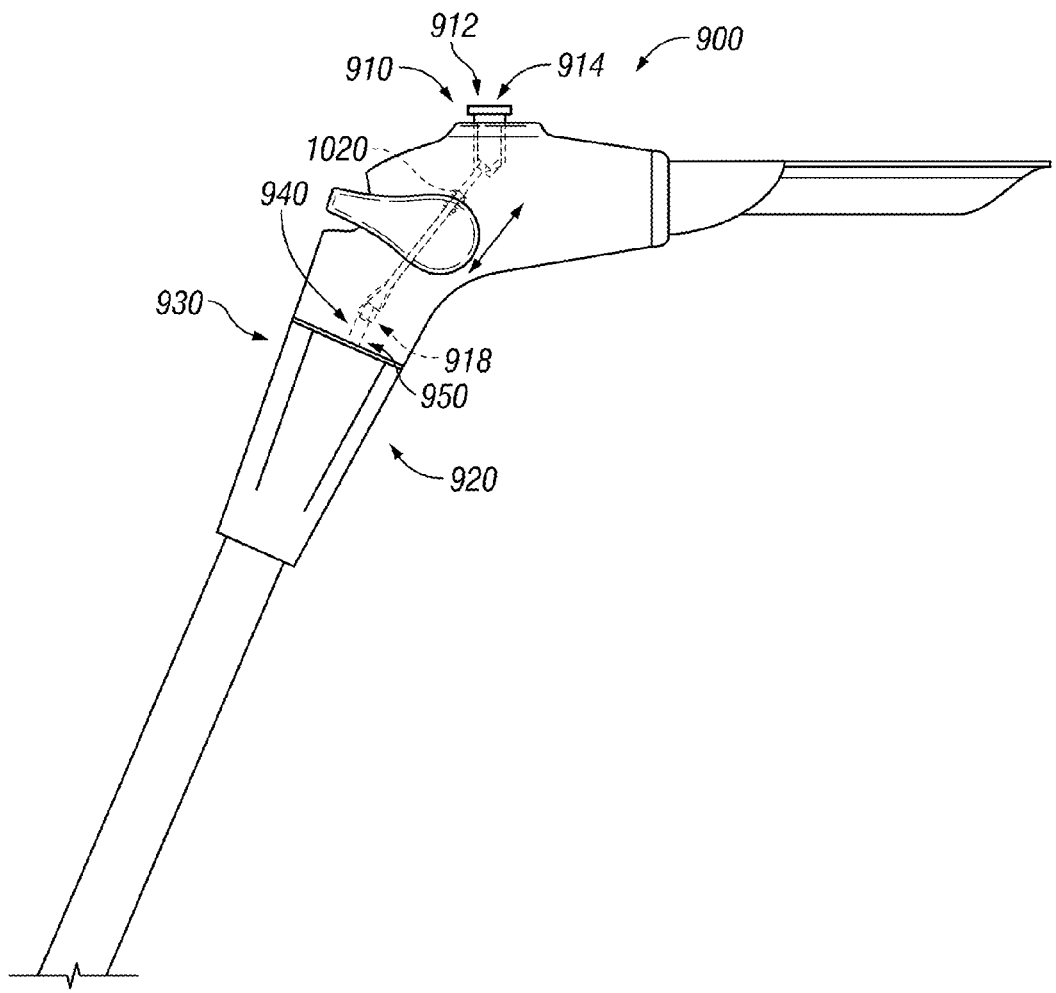
FIG. 12 is a side elevational view of an embodiment of an AWV instrument including a detachable head, and also shown an embodiment of an automatic shut-off mechanism.
Figure 13:
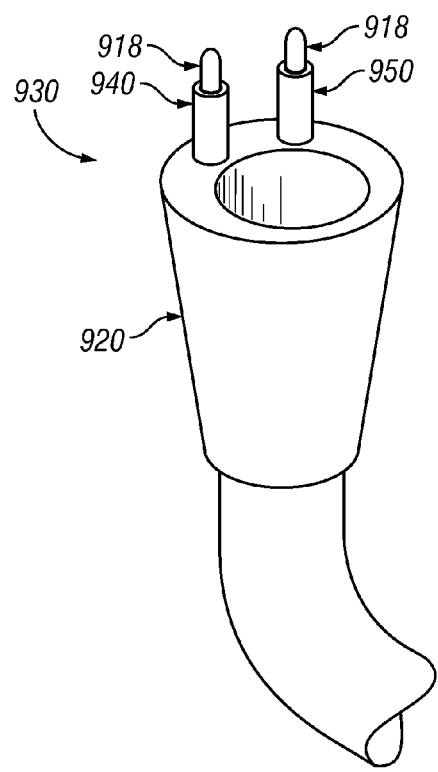

As shown in FIG. 12, the head 910 of the AWV instrument 900 is removably attachable to handle/grip 920 so that the head 910 may be removed for cleaning and sterilization of the head 910 because waste (i.e. saliva/debris) and water supply are transmitted through reusable head 910.

Figure 14A:
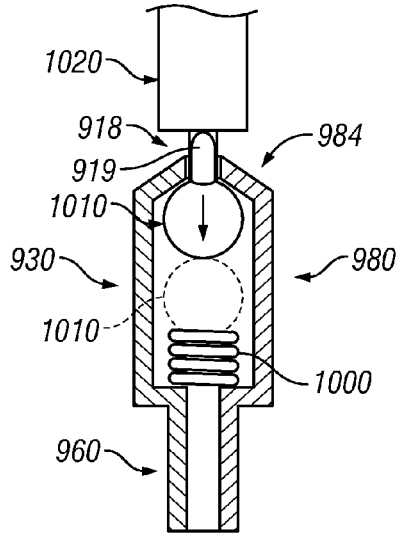
FIG. 14A is a cross-sectional view of an embodiment of the automatic shut-off mechanism of the AWV instrument of FIG. 12, and shows the automatic shut-off mechanism in a first condition.
Figure 14B:
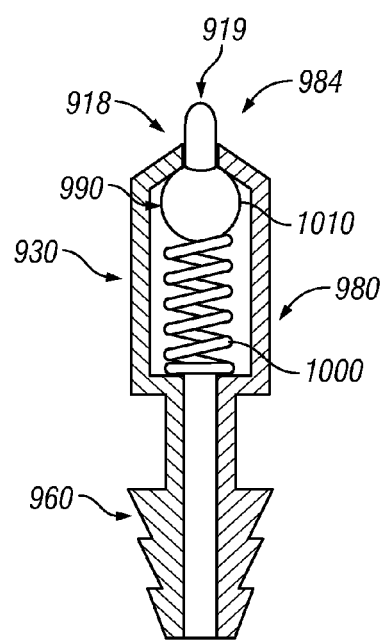
FIG. 14B is a cross-sectional view of the automatic shut-off mechanism of FIG. 12, and shows the automatic shut-off mechanism in a second condition.

With reference to FIGS. 12-14B, in an embodiment of an automatic shut-off valve mechanism 930, the head 910 includes air and water buttons 912, 914 that push on linkage rod(s) 1020. Linkage rod(s) 1020 push poppet valve(s) 918. Pushing on the air/water buttons 912, 914 causes air/water to flow through the poppet valve(s) 918 and past the linkage rod(s) 1020 and into air/water channels (not shown) that direct air/water into the tip. When the air/water buttons 912, 914 are released, spring(s) 1000 on the poppet valve(s) 918 urge the poppet valve(s) 918 back into position, into a sealing relationship to create an automatic seal or shut-off. The linkage rod(s) 1020 eliminate the need for additional valves/O-rings and corresponding maintenance. The poppet valve(s) 918 are disposed in lower water tube connector 940 and lower air tube connector 950. The connectors 940, 950 include an anchor 960 connected to handle/grip member 920 and cylindrical chamber 980 with an upper open end 984. The cylindrical chamber 980 includes a valve seat 990 with spring 1000 and a ball (rubber or metal) 1010 thereon. The buttons 70, 80 are actuated to cause the linkage rod(s) to push poppet actuator(s) 919 of the poppet valve(s) 918 so that the ball 1010 is pressed downward for water/air release. As shown in FIG. 14B, when the linkage rod 1020 is withdrawn (e.g., when the head 910 is removably attachable to handle/grip 920), the spring 1000 urges the ball 1010 into a sealing relationship with upper open end 984 to create an automatic seal or shut-off in the lower water tube connector 940 and lower air tube connector 950.

The above figures may depict exemplary configurations for the invention, which is done to aid in understanding the features and functionality that can be included in the invention. The invention is not restricted to the illustrated architectures or configurations, but can be implemented using a variety of alternative architectures and configurations. Additionally, although the invention is described above in terms of various exemplary embodiments and implementations, it should be understood that the various features and functionality described in one or more of the individual embodiments with which they are described, but instead can be applied, alone or in some combination, to one or more of the other embodiments of the invention, whether or not such embodiments are described and whether or not such features are presented as being a part of a described embodiment. Thus the breadth and scope of the present invention, especially in any following claims, should not be limited by any of the above-described exemplary embodiments.

Terms and phrases used in this document, and variations thereof, unless otherwise expressly stated, should be construed as open ended as opposed to limiting. As examples of the foregoing: the term "including" should be read as mean "including, without limitation" or the like; the term "example" is used to provide exemplary instances of the item in discussion, not an exhaustive or limiting list thereof; and adjectives such as "conventional," "traditional," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although item, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

We claim:
1. An air water vacuum dental instrument, comprising:
a handle;
a head;
an air control carried by at least one of the handle and the head;

a water control carried by at least one of the handle and the head;

a vacuum control carried by at least one of the handle and the head, the vacuum control including a vacuum control valve carried by the head and a lever to control the valve;

an air water vacuum tip coupled to the head and configured to provide at least air, water, and vacuum in a mouth of a dental patient at the air water vacuum tip;

the head having a first communication passage which communicates with the air water vacuum tip and a second communication passage which is configured to communicate with a vacuum source;

the vacuum control valve being located between the first and second communication passages and including a periphery with a pair of high flow rate evacuator ports and a single, low flow rate saliva ejector port in communication with the pair of high flow rate evacuator ports;

wherein the vacuum control valve is configured for rotation between a high-flow vacuum condition in which the pair of high flow rate evacuator ports communicate with the first and second communication passages, a low-flow vacuum condition in which one of the high flow rate evacuator ports is in partial communication with one of the communication passages and the low flow rate saliva ejector port is in communication with the other communication passage, and a no-flow vacuum condition in which the pair of high flow rate evacuator ports and low flow rate saliva ejector port are blocked from communication with the first and second communication passages.

2. The air water vacuum dental instrument of claim 1, further including
an auto-shutoff mechanism that automatically shuts off the vacuum in the mouth of the dental patient on detection of at least partial blocking of the air water vacuum tip.

3. The air water vacuum dental instrument of claim 2, wherein the auto-shutoff mechanism includes a normal condition where a suction force overcomes an opposing force to allow the vacuum in the mouth of the dental patient and a shut-off condition where the opposing force overcomes the suction force to shut off the vacuum in the mouth of the dental patient.

4. The air water vacuum dental instrument of claim 3, wherein the auto-shutoff mechanism includes at least one spring to provide the opposing force.

5. The air water vacuum dental instrument of claim 3, wherein the auto-shutoff mechanism includes at least one magnet to provide the opposing force.

6. The air water vacuum dental instrument of claim 1 further including a rotatable tip positioner that rotatably couples the air water vacuum tip to the head to provide at least air, water, and vacuum in a mouth of a dental patient at the air water vacuum tip.

7. The air water vacuum dental instrument of claim 1, further including a spring that urges the vacuum control to the no-flow vacuum condition.

8. The air water vacuum dental instrument of claim 1, wherein the vacuum control includes a rotatable trigger valve barrel and a trigger carried by the handle, the trigger operably associated with the rotatable trigger valve barrel to rotate the trigger valve barrel to a different flow condition with each pull of the trigger.

9. The air water vacuum dental instrument of claim 1, wherein the vacuum control includes a high flow rate suction trigger and a lower flow rate evacuator toggle carried by the handle.

10. The air water vacuum dental instrument of claim 1 further including a hose connected to the handle and delivering water and air therethrough, at least one of the hose, the handle, and the head including one or more heating elements to heat at least one of the water and the air.

11. The air water vacuum dental instrument of claim 9, wherein the hose includes a heating lumen, an adjacent water lumen, and an adjacent air lumen, and the heating lumen includes one or more heating elements to heat the water in the water lumen and the air in the air lumen.

12. The air water vacuum dental instrument of claim 1, wherein the head is removably coupled to the handle.

13. The air water vacuum dental instrument of claim 12, further including a quick-release mechanism that is actuatable to decouple the head from the handle.

14. The air water vacuum dental instrument of claim 12, wherein the head is at least one of sterilizable and autoclavable.

15. The air water vacuum dental instrument of claim 1, wherein the air water vacuum tip is configured to bend at least one of water and air emitted at the tip.

16. The air water vacuum dental instrument of claim 15, wherein the air water vacuum tip includes a distal vertex, a proximate vertex with at least one of air and water emitted therefrom, and a vacuum port therebetween, at least one of water and air emitted at the proximate vertex bending towards the vacuum port during vacuum.

17. The air water vacuum dental instrument of claim 1, wherein the air water vacuum tip includes a distal vertex with at least one of air and water emitted therefrom, a proximal vertex, and a vacuum port therebetween, at least one of water and air emitted straight at the distal vertex without bending towards the vacuum port during vacuum.

18. The air water vacuum dental instrument of claim 1, wherein the head is removably coupled to the handle and the air water vacuum dental instrument includes an automatic water shut-off valve mechanism that automatically shuts off water flow upon decoupling of the head from the handle and an automatic air shut-off valve mechanism that automatically shuts off air flow upon decoupling of the head from the handle.

* * * * *